United States Patent
Hasegawa et al.

(10) Patent No.: US 7,795,505 B2
(45) Date of Patent: Sep. 14, 2010

(54) HERBICIDE-RESISTANCE GENE AND UTILIZATION THEREOF

(75) Inventors: Hisakazu Hasegawa, Atsugi (JP); Teruhiko Terakawa, Atsugi (JP); Kiyoshi Hirazawa, Tokyo (JP)

(73) Assignee: Hokko Chemical Industry Co., Ltd., Chuo-ku, Tokyo (JP)

( * ) Notice: Subject to any disclaimer, the term of this patent is extended or adjusted under 35 U.S.C. 154(b) by 557 days.

(21) Appl. No.: 11/719,509

(22) PCT Filed: Nov. 8, 2005

(86) PCT No.: PCT/JP2005/020439
§ 371 (c)(1),
(2), (4) Date: May 16, 2007

(87) PCT Pub. No.: WO2006/054458
PCT Pub. Date: May 26, 2006

(65) Prior Publication Data
US 2009/0158469 A1 Jun. 18, 2009

(30) Foreign Application Priority Data
Nov. 17, 2004 (JP) .............................. 2004-333131

(51) Int. Cl.
*A01H 5/10* (2006.01)
*C12N 15/52* (2006.01)
*C12N 15/82* (2006.01)
*C12N 9/10* (2006.01)

(52) U.S. Cl. .................... 800/300; 435/193; 435/320.1; 435/419; 536/23.2; 800/298

(58) Field of Classification Search .................. None
See application file for complete search history.

(56) References Cited
FOREIGN PATENT DOCUMENTS

| | | |
|---|---|---|
| JP | 63-71183 | 3/1988 |
| JP | 02-171188 | 2/1990 |
| JP | 2539901 B | 7/1996 |
| JP | 9-107981 | 4/1997 |
| JP | 10-080289 | 3/1998 |
| JP | 3062125 B | 4/2000 |

OTHER PUBLICATIONS

Spencer et al 1992, Plant Molecular Biology 18: 201-210.*
Strauch, et al. "Cloning of a Phosphinothricin N- acetyltransferase Gene from *Streptomyces viridochromogenes* Tü494 and Its Expression in *Streptomyces lividans* and *Escherichia coli*," *Gene*, vol. 63, pp. 65-74, 1988.
Murakami, et al. "The Bialaphos Biosynthetic Genes of *Streptomyces hygroscopicus*: Molecular Cloning and Characterization of the Gene Cluster," *Molecular General Genetics*, vol. 205, pp. 42-50, 1986.
Thompson, et al. "Characterization of the Herbicide-Resistance Gene *bar* from *Streptomyces hygroscopicus*," *EMBO Journal*, vol. 6, No. 9, pp. 2519-2523, 1987.
Bedford, et al. "Characterization of a Gene Conferring Bialaphos Resistance in *Streptomyces coelicolor* A3(2)," *Gene*, vol. 104, pp. 39-45, 1991.
Omura, et al. "Accession: BAC71407 (gi: 29607349), Definition: Putative Phosphinothricin N-Acetyltransferase (*Streptomyces avermitilis*)," NCBI Sequence Revision History (online): Apr. 7, 2003.
Marcos, et al. "Three Genes *hrdB*, *hrdD* and *hardT* of *Streptomyces griseus* IMRU 3570, Encoding Sigma Factor-Like Proteins, Are Differentially Expressed Under Specific Nutritional Conditions," *Gene*, vol. 153, pp. 41-48, 1995.
International Search Report dated Dec. 22, 2005.

* cited by examiner

*Primary Examiner*—David H Kruse
(74) *Attorney, Agent, or Firm*—Knobbe, Martens, Olson & Bear, LLP (57) ABSTRACT

A DNA encoding a phosphinothricin acetyltransferase protein obtained from *Streptomyces* sp. AB3534 strain is described which imparts a resistance to herbicides, particularly the herbicide phosphinothricin (PPT). Plants having a herbicide resistance are constructed by transforming a plant cell with DNA encoding the phosphinothricin acetyltransferase protein and then regenerating the transformed plant cell into a plant. A recombinant protein having the herbicide-resistant activity is also described.

12 Claims, 1 Drawing Sheet

SEQUENCE LISTING

```
<160> NUMBER OF SEQ ID NOS: 5

<210> SEQ ID NO 1
<211> LENGTH: 617
<212> TYPE: DNA
<213> ORGANISM: Streptomyces sp. AB3534
<220> FEATURE:
<221> NAME/KEY: CDS
<222> LOCATION: (68)..(592)

<400> SEQUENCE: 1
gaattcccaa cccgcgcctg gattttctg atcatgcagt accctgtcgc accacacggg      60 agggctg atg cgg tca gaa cgt aca gat gtg cag gtc agg cct gga gtg     109
        Met Arg Ser Glu Arg Thr Asp Val Gln Val Arg Pro Gly Val
          1               5                  10 gcg gcc gat ctc gat gca ctc acg gac ctc tac aac cac tac gta cgt    157
Ala Ala Asp Leu Asp Ala Leu Thr Asp Leu Tyr Asn His Tyr Val Arg
 15              20                  25                  30 gag acg ccg atc aca ttc gac acc gat gtg ttc acc tcc gga caa cgc    205
Glu Thr Pro Ile Thr Phe Asp Thr Asp Val Phe Thr Ser Gly Gln Arg
                 35                  40                  45 cgt ccg tgg ctg ctc tcc cac cct gaa gac gga ccg cac cgt ctg atg    253
Arg Pro Trp Leu Leu Ser His Pro Glu Asp Gly Pro His Arg Leu Met
             50                  55                  60 gtt gcc acg gac acg gat tca cag gtg att ctg ggg tac gcc acg tcc    301
Val Ala Thr Asp Thr Asp Ser Gln Val Ile Leu Gly Tyr Ala Thr Ser
             65                  70                  75 agc gcc ttt ccg gcg aag ccc gcc tac gcg acc tcc gtg gag gtg acg    349
Ser Ala Phe Pro Ala Lys Pro Ala Tyr Ala Thr Ser Val Glu Val Thr
         80                  85                  90 gtc tac gtc gct ccg gac gcg ggg cga cga ggc atc ggc acc ctc ctc    397
Val Tyr Val Ala Pro Asp Ala Gly Arg Arg Gly Ile Gly Thr Leu Leu
 95                 100                 105                 110 tac caa gcg ctg ttc tcg gcg ctc gcc ggc gag gac ctg cac cgg gcc    445
Tyr Gln Ala Leu Phe Ser Ala Leu Ala Gly Glu Asp Leu His Arg Ala
                115                 120                 125 tac gcg ggc atc gcg ctg ccg aac gag ggg tcg gtg cgc ctg cac gaa    493
Tyr Ala Gly Ile Ala Leu Pro Asn Glu Gly Ser Val Arg Leu His Glu
            130                 135                 140 cgc ttc ggg ttc cgg cac gtc ggc acc tac cgg gag gtc ggc cgg aag    541
Arg Phe Gly Phe Arg His Val Gly Thr Tyr Arg Glu Val Gly Arg Lys
        145                 150                 155 ttc ggc cgc tac tgg gac gtc gcc tgg tac gag aag gaa ctc ccc cac    589
Phe Gly Arg Tyr Trp Asp Val Ala Trp Tyr Glu Lys Glu Leu Pro His
    160                 165                 170 tag cgaacgcccc cacccggaac ccggg                                    617

<210> SEQ ID NO 2
<211> LENGTH: 174
<212> TYPE: PRT
<213> ORGANISM: Streptomyces sp. AB3534

<400> SEQUENCE: 2

Met Arg Ser Glu Arg Thr Asp Val Gln Val Arg Pro Gly Val Ala Ala
              5                  10                  15
```

```
Asp Leu Asp Ala Leu Thr Asp Leu Tyr Asn His Tyr Val Arg Glu Thr
             20                  25                  30
Pro Ile Thr Phe Asp Thr Asp Val Phe Thr Ser Gly Gln Arg Arg Pro
             35                  40                  45
Trp Leu Leu Ser His Pro Glu Asp Gly Pro His Arg Leu Met Val Ala
 50                  55                  60
Thr Asp Thr Asp Ser Gln Val Ile Leu Gly Tyr Ala Thr Ser Ser Ala
 65                  70                  75                  80
Phe Pro Ala Lys Pro Ala Tyr Ala Thr Ser Val Glu Val Thr Val Tyr
             85                  90                  95
Val Ala Pro Asp Ala Gly Arg Arg Gly Ile Gly Thr Leu Leu Tyr Gln
            100                 105                 110
Ala Leu Phe Ser Ala Leu Ala Gly Glu Asp Leu His Arg Ala Tyr Ala
            115                 120                 125
Gly Ile Ala Leu Pro Asn Glu Gly Ser Val Arg Leu His Glu Arg Phe
            130                 135                 140
Gly Phe Arg His Val Gly Thr Tyr Arg Glu Val Gly Arg Lys Phe Gly
145                 150                 155                 160
Arg Tyr Trp Asp Val Ala Trp Tyr Glu Lys Glu Leu Pro His
            165                 170

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 3 gagtttgatcctggctca                                                      18

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 4
gctctagaga tgcggtcaga acgtac                                            26

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 5
gcgagctcgg cgttcgctag tgg                                               23
```

HERBICIDE-RESISTANCE GENE AND UTILIZATION THEREOF

RELATED APPLICATIONS

This is the U.S. National Phase under 35 U.S.C. §371 of International Application PCT/JP2005/020439, filed Nov. 8, 2005, which was published in a language other than English, which claims priority of JP Application No. 2004-333131, filed Nov. 17, 2004.

TECHNICAL FIELD

The present invention relates to a herbicide-resistance gene and utilization thereof, and more specifically to a protein involved in a resistance to herbicides and a novel gene encoding the protein. Moreover, the present invention relates to a plant cell, a plant body, and a seed which are transformed by the gene.

BACKGROUND ART

In recent years, herbicide-resistant plants that are not affected by herbicides have been developed using genetic engineering techniques. A herbicide, phosphinothricin (PPT), is used as a nonselective herbicide, and the action mechanism thereof is as follows: PPT is absorbed in a plant body, and then PPT inhibits a glutamine synthase and causes accumulation of $NH_3$ harmful to plant bodies, resulting in plant death.

Phosphinothricin acetyl transferase gene is known as a gene involved in a resistance to PPT, and gene products thereof are known to acetylate PPT by an enzymatic reaction, to thereby deactivate the herbicide effect.

Examples of PPT resistance gene include:

(1) a phosphinothricin acetyltransferase gene obtained from *Streptomyces viridochromogenes* (Patent Documents 1, 2, and 3, and Non-patent Document 1);

(2) a phosphinothricin acetyltransferase gene obtained from *Streptomyces hygroscopicus* (Non-patent Documents 2 and 3), (3) a phosphinothricin acetyltransferase gene obtained from *Actinomyces* AB2253 strain (Patent Document 4);

(4) a phosphinothricin acetyltransferase gene obtained from *Streptomyces coelicolor* (Non-patent Document 4);

(5) a phosphinothricin acetyltransferase gene obtained from *Escherichia coli* (NCBI No. 7427901);

(6) a phosphinothricin acetyltransferase gene obtained from *Agrobacterium tumefaciens* (NCBI No. 17739287); and (7) a phosphinothricin acetyltransferase gene obtained from *Bacillus subtilis* (NCBI No. 2636181).

Patent Document 1: JP 63-71183 A
Patent Document 2: JP 3062125 B
Patent Document 3: JP 9-107981 A
Patent Document 4: JP 2539901 B
Non-patent Document 1: "Gene", 1988, vol. 63, pp. 65-74
Non-patent Document 2: "Molecular General Genetics", 1986, vol. 205, pp. 42-50
Non-patent Document 3: "The EMBO Journal", 1987, vol. 6, pp. 2519-2523
Non-patent Document 4: "Gene", 1991, vol. 104, pp. 39-45

DISCLOSURE OF THE INVENTION

An object of the present invention is to provide a novel herbicide-resistance gene and to provide a protein encoded by the gene.

The inventors of the present invention have made extensive studies to achieve the above-described object. As a result, the inventors of the present invention have succeeded in construction of a resistance gene to the herbicide phosphinothricin (PPT) and a transformant having an enhanced resistance to herbicides by introduction of the gene as described below. That is, the gist of the present invention is as follows:

(1) A protein shown in the following (A) or (B):
  (A) a protein having the amino acid sequence represented by SEQ ID NO: 2;
  (B) a protein having an amino acid sequence of SEQ ID NO: 2 including substitution, deletion, insertion, or addition of one or plural amino acids and having a herbicide-resistant activity;

(2) a DNA encoding a protein shown in the following (A) or (B):
  (A) a protein having the amino acid sequence represented by SEQ ID NO: 2;
  (B) a protein having an amino acid sequence of SEQ ID NO: 2 including substitution, deletion, insertion, or addition of one or plural amino acids and having a herbicide-resistant activity;

(3) the DNA, which is shown in the following (a) or (b):
  (a) a DNA having nucleotides 68 to 592 in the nucleotide sequence represented by SEQ ID NO: 1;
  (b) a DNA hybridizing with a DNA having nucleotides 68 to 592 in the nucleotide sequence represented by SEQ ID NO: 1 or with a probe that can be prepared from the nucleotides under stringent conditions;

(4) a recombinant vector including the DNA;

(5) a transformed plant cell which is transformed by the DNA or by the recombinant vector;

(6) a transformed plant which is transformed by the DNA or by the recombinant vector;

(7) a seed which is obtained from the transformed plant; and (8) a herbicide-resistant plant body which is transformed with the DNA or by the recombinant vector, and exhibits a resistance to herbicides by expressing the DNA or the DNA in the recombinant vector.

BEST MODE FOR CARRYING OUT THE INVENTION

Hereinafter, the present invention will be described in detail.

A protein of the present invention is shown in the following (A) or (B).

(A) A protein having the amino acid sequence represented by SEQ ID NO: 2.

(B) A protein having an amino acid sequence of SEQ ID NO: 2 including substitution, deletion, insertion, or addition of one or plural amino acids and having a herbicide-resistant activity.

A protein having the amino acid sequence represented by SEQ ID NO: 2 is a protein encoded by a gene obtained from an actinomycete strain named *Streptomyces* sp. AB3534 as a gene involved in the resistance to herbicides.

A person skilled in the art widely recognizes that, in general, if one or plural amino acids are substituted, deleted, inserted, or added in an amino acid sequence encoding a protein having a particular function or physiological activity, the function or physiological activity may be maintained. The present invention encompasses a protein having such modification and having a herbicide-resistant activity. That is, the present invention encompasses a protein having an amino acid sequence of SEQ ID NO: 2 in Sequence Listing including substitution, deletion, insertion, or addition of one or plural amino acids and having a herbicide-resistant activity. Such a modified protein can be obtained by introducing a mutation into a DNA encoding the amino acid sequence represented by SEQ ID NO: 2 by, for example, the site-specific mutation so that an amino acid on a specific site is deleted, substituted, or added.

The term "plural" refers to a number in the range of preferably 2-25, more preferably 2-10, particularly preferably 2-5. Alternatively, the term "plural" refers to such a number that the homology to the amino acid sequence represented by SEQ ID NO: 2 is corresponding to preferably 85% or more, more preferably 90% or more, particularly preferably 95% or more.

The protein of the present invention can be produced by expressing the DNA of the present invention to be described below in an appropriate host. Examples of the host include bacteria such as *Escherichia coli* and *Bacillus subtilis*, Yeasts, cultured insect cells, cultured animal cells, and cultured plant cells. The DNA of the present invention is expressibly ligated downstream of an expression regulation sequence such as a promoter that functions in host cells, to thereby transform the host cells. Such transformation can be carried out by: constructing a recombinant plasmid by ligating the DNA of the present invention to a plasmid; and introducing the resultant recombinant plasmid into a host. Alternatively, a host can be transformed by integrating the DNA of the present invention into a chromosomal DNA in a host by homologous recombination and the like. If the resultant transformed cells are cultured under conditions that allow the promoter expression regulation sequence to function, a protein of the present invention is produced.

The DNA of the present invention is a DNA encoding the above-described protein (A) or (B) of the present invention. Examples of the DNA encoding the protein (A) include a DNA having nucleotides 68 to 592 in the nucleotide sequence represented by SEQ ID NO: 1.

Meanwhile, examples of the DNA encoding the protein (B) include a DNA that hybridizes with a DNA having nucleotides 68 to 592 in the nucleotide sequence represented by SEQ ID NO: 1 or with a probe that can be prepared from the nucleotides under stringent conditions. The term "stringent conditions" used herein refers to conditions that allow formation of so-called a specific hybrid and do not allow formation of a non-specific hybrid. Specifically, the conditions include conditions that allow hybridization of two nucleic acids having high homology, that is, two DNAs having, for example, 70% or more, preferably 80%, more preferably 90%, particularly preferably 95% or more homology and do not allow hybridization of two nucleic acids having homology lower than the above levels. More specifically, the conditions include conditions that allow hybridization of nucleic acids in a hybridization solution (500 mM NaPi buffer (pH 7.2), 7% SDS, 1 mM EDTA) at 68° C.

The above-mentioned DNA encoding the protein (B) can be obtained by: subjecting a DNA encoding the protein (A) or cells containing the DNA to a mutation treatment; and selectively separating a DNA that hybridizes with a DNA having nucleotides 68 to 592 in the nucleotide sequence represented by SEQ ID NO: 1 in Sequence Listing under stringent conditions from the mutated DNAs or the cells including thereof.

In a process for completing the present invention, the DNA encoding the protein (A) is a DNA isolated from a bacterial strain that is selected as a bacterial strain capable of growing by inoculating an actinomycete into a selective medium containing bialaphos, as described in Examples below, and belongs to the genus *Streptomyces*. Note that bialaphos is taken into cells, and then converted into active PPT by hydrolysis. The bacterial strain was named *Streptomyces* sp. AB3534, and deposited at the National Institute of Advanced Industrial Science and Technology (Central 6, 1-1-1 Higashi, Tsukuba, Ibaraki, Japan) on Oct. 26, 2004 with accession number FERM P-20273. Then, the strain was transferred to international deposit under the Budapest Treaty on Oct. 5, 2005 with accession number FERM BP-10430.

The DNA encoding the protein (A) can be isolated from chromosomal DNA of the AB3534 strain or an actinomycete closely related to the strain by PCR or hybridization using oligonucleotides prepared based on the nucleotide sequence represented by SEQ ID NO: 1 as primers or probes.

A transformant of *Escherichia coli* carrying the DNA of the present invention can grow in a medium containing bialaphos at a concentration that does not allow untransformed strains to grow.

*Escherichia coli* JM109 transformed with a plasmid pUC18-B2 containing the DNA encoding the protein (A) was named *Escherichia coli* JM109/pUC18-B2, and deposited at the National Institute of Advanced Industrial Science and Technology (Central 6, 1-1-1 Higashi, Tsukuba, Ibaraki, Japan) on Oct. 26, 2004 with accession number FERM P-20272. Then, the strain was transferred to international deposit under the Budapest Treaty on Oct. 5, 2005 with accession number FERM BP-10429.

If the DNA of the present invention or a recombinant vector containing it is introduced into plant cells so that the DNA of the present invention can be expressed, the resistance to herbicides can be imparted to the plant cells or a plant body regenerated from the cells.

The DNA of the present invention can be introduced into plant cells by an established known method ("Saibo Kogaku (Cell Engineering), suppl. vol. Protocol for Experiments Using Model Plants, Rice/Arabidopsis", pp. 78-81 (1996), published by Shujunsha Co. Ltd.), and examples of the method include the Agrobacterium method, whisker inducing method, electroporation method, and particle gun method.

Meanwhile, a promoter for expressing the DNA of the present invention in plant cells may be one that causes expression in plant cells, and examples thereof include a ubiquitin promoter ("Plant Molecular Biology" 1992, vol. 18 pp. 675-689) and CaMV35S promoter ("The EMBO J.", vol. 6, pp. 3901-3907 (1987)). Moreover, examples of a plasmid including a promoter that functions in plant cells include pUBA ("Plant Molecular Biology" 1992, vol. 18, 675-689) and pIG121Hm ("Plant Cell Phisiology" 1990, vol. 31, pp. 805-

813). The promoter for expressing the DNA of the present invention may be a constitutive promoter or an inducible promoter.

Examples of a plant applicable to the present invention include, but are not limited to, monocotyledons such as rice, corn, wheat, barley, turf grass, and other monocotyledons; or dicotyledons such as soybean, cotton, rapeseed, potato, sugar beet, Arabidopsis, tobacco, tomato, Chinese cabbage, and cucumber. Regeneration of a plant body from plant cells can be carried out by a known method ("Plant Journal" 1994, vol. 6, 271-282).

Only transformed cells can be selected by culturing cells introduced with a gene on a medium containing bialaphos or PPT for a certain period of time. Meanwhile, a plant body having a resistance to herbicides can be regenerated by culturing the selected cells on a medium containing bialaphos or PPT for a certain period of time.

Seeds of a plant carrying the DNA of the present invention can be obtained by collecting seeds from a plant body carrying the DNA of the present invention obtained as described above.

EXAMPLES

Hereinafter, the present invention will be described in more detail by way of examples.

Example 1

Cloning of a Herbicide-Resistance Gene (1) Screening of Herbicide-Resistant Bacteria Actinomycetes (about 500 strains) stored by the applicant of the present invention were inoculated into a selective medium containing bialaphos and cultured at 27° C. for 7 days, and then the growth conditions of the respective bacteria were investigated. The selective medium is an agar medium prepared by pouring 20 ml of a medium obtained by adding 50 mg/l of bialaphos to a medium having the composition of 1% glucose, 0.2% L-asparagine, 0.03% NaCl, 0.05% $MgSO_4.7H_2O$, 0.5% (V/V) a trace element solution (a solution of 40 mg of $ZnCl_2$, 200 mg of $FeCl_3.6H_2O$, 20 mg of $CuCl_2.2H_2O$, 20 mg of $MnCl_2.4H_2O$, 20 mg of $(NH_4)_6Mo_7O_{24}.4H_2O$, 20 mg of $CoCl_2.6H_2O$, and 100 mg of $CaCl_2.2H_2O$ in 1 L of water), and 1.8% Bacto-agar into a plastic petri dish with a diameter of 9 cm, and solidifying the medium.

As a result, AB3534 strain was selected as a bacterial strain capable of growing on the selective medium. The taxonomic characteristics of AB3534 strain obtained by the above-described screening are shown below. Note that the experiments were carried out in accordance with the method described in "Classification and Identification of Actinomycetes" (Business center for Academic Societies Japan, 2001).

(a) Analysis of Bacterial Cell

Diaminopimelic acid in a hydrolysate of all bacterial cells was found to be LL isomer.

(b) Analysis of 16S rRNA Gene

The homology of the nucleotide sequence of 16S ribosome RNA was examined as follows: a sequence including 586 nucleotides was determined using a primer having the sequence represented by SEQ ID NO: 3 and compared to data of known bacterial strains registered on the DNA database. As a result, the nucleotide sequence of the above-described bacterial strain was found to have high homology to the nucleotide sequences of 16S rRNAs of actinomycetes belonging to the genus *Streptomyces*.

TABLE 1

| Bacterial strain | Homology of 16S rRNA sequence (%) |
|---|---|
| *Streptomyces olivochromogenes* (*S. olivochromogenes*) | 99.5% |
| *Streptomyces griseochromogenes* (*S. griseochromogenes*) | 99.3% |
| *Streptomyces galilaeus* (*S. galilaeus*) | 99.3% |
| *Streptomyces resistomycificus* (*S. resistomycificus*) | 99.3% |
| *Streptomyces chartreuses* (*S. chartreuses*) | 99.3% |

The results identified the above-described bacterial strain as an actinomycete strain belonging to the genus *Streptomyces*. The actinomycete AB3534 strain was named *Streptomyces* sp. AB3534.

(2) Preparation of Hybrid Plasmid

*Streptomyces* sp. AB3534 was cultured in a 500-ml Sakaguchi flask containing 100 ml of TRYPTIC SOY BROTH (manufactured by DIFCO) at 27° C. for 3 days. The culture solution was centrifuged at 6,000 rpm for 15 minutes to collect the bacterial cells, and then the cells were freeze-dried and pulverized in a mortar. From the pulverized cells, total DNA was extracted using DNeasy Plant Maxi Kit (manufactured by QIAGEN). The resultant DNA (5 μg) was treated with 20 units of a restriction enzyme BglII at 37° C. for 2 hours, to thereby yield DNA fragments. On the other hand, 1 μg of the DNA of a plasmid pIJ703 obtained by extraction and purification from bacterial cells of *Streptomyces lividans* 3131 (ATCC 35287) was cleaved with BglII in the same way as described above. The both fragments were purified using GeneClean (manufactured by Bio101) and allowed to react using Takara Ligation kit (manufactured by Takara Bio Inc.) at 16° C. for 3 hours, to thereby yield a mixture of various hybrid plasmids obtained by integrating BglII-cleaved fragments of total DNA of *Streptomyces* sp. AB3534 into BglII-cleaved DNA fragments of the plasmid pIJ703.

(3) Detection and Cloning of Herbicide-Resistance Gene

The hybrid plasmid mixture thus obtained was used to transform a protoplast of *Streptomyces lividans*. The protoplast was regenerated, and then transformed strains having a bialaphos resistance were selected on a selective medium containing 10 mg/L bialaphos. The *Streptomyces lividans* used above as a host is a bacterial strain obtained by removing a plasmid pIJ703 from *Streptomyces lividans* 3131 by protoplastization and regeneration. *Streptomyces lividans* 3131 was obtained from Department of Antibiotics, National Institute of Health in 1985 ("The Journal of Antibiotics" 1985, vol. 38, pp. 390-400).

The above-described protoplast of *Streptomyces lividans* used for transformation was prepared as follows. *Streptomyces lividans* was inoculated into 25 ml of a medium having a composition containing 1% glucose, 0.4% polypeptone (manufactured by DIFCO), 0.4% yeast extract (manufactured by DIFCO), 0.05% $MgSO_4.7H_2O$, 0.1% $K_2HPO_4$, and 0.05% glycine, and the medium was transferred to a 100-ml Sakaguchi flask together with a stainless-steel spring with a length of 1.5 cm and a diameter of 1 cm, followed by culture at 27° C. for 2 days. The culture solution (2 ml) was added to a 500-ml Sakaguchi flask containing 100 ml of a medium having a composition containing 1% glucose, 0.3% yeast extract (manufactured by DIFCO), 0.5% bacto peptone (manufactured by DIFCO), 0.3% malt extract (manufactured by DIFCO), 34% sucrose, 0.1% $MgCl_2 6H_2O$, and 0.5% glycine, and further cultured at 27° C. for 2 days. The culture solution (5 ml) was centrifuged at 8,000 rpm for 10 minutes to collect the bacterial cells, and the cells were washed with a 0.5 M sucrose solution and suspended in 4 ml of a buffer having a composition containing 70 mM NaCl, 5 mM $MgCl_2$, 5 mM $CaCl_2$, 0.4 M sucrose, 25 mM Good's TES buffer (pH 7.2).

To the cell suspension was added 100 µl of a 40 mg/ml egg-white lysozyme solution, followed by incubation at 30° C. for 90 minutes, to thereby yield a protoplast. The cells which did not become protoplast were removed by cotton-filtration, and the filtrate was centrifuged at 3,500 rpm for 10 minutes to collect the protoplast. The collected protoplast was washed once with a buffer (PWP buffer) having a composition containing 70 mM NaCl, 10 mM $MgCl_2$, 20 mM $CaCl_2$, 0.4 M sucrose, and 25 mM Good's TES buffer (pH 7.2), and then suspended in the buffer to about $1 \times 10^9$ cells/ml.

To 250 µl of the protoplast suspension were added 50 µl of the hybrid plasmid mixture solution obtained the item (1) above and 300 µl of a 40% polyethylene glycol 4000 (manufactured by Wako Pure Chemical Industries, Ltd.), and the mixture was allowed to stand on ice for 2 minutes. Then, 900 µl of the above-described PWP buffer was added to decrease the concentration of polyethylene glycol. The mixed solution (150 µl) was applied to an agar medium (1% glucose, 0.05% KCl, 0.01% $K_2HPO_4$, 0.2% $MgCl_2.6H_2O$, 0.07% $CaCl_2.2H_2O$, 0.1% polypeptone (manufactured by DIFCO), 0.4% yeast extract (manufactured by DIFCO), 0.5% (V/V) a trace element solution, 25 mM Good's TES buffer (pH 7.2), and 1.8% bacto agar (manufactured by DIFCO)), which was obtained by dispensing and solidifying the medium in a plastic petri dish with a diameter of 9 cm, followed by culture at 27° C. for 10 days to regenerate the protoplast and form aerial mycelia. Note that the trace element solution is an aqueous solution containing 40 mg of $ZnCl_2$, 200 mg of $FeCl_3.6H_2O$, 20 mg of $CuCl_2.2H_2O$, 20 mg of $MnCl_2.4H_2O$, 20 mg of $(NH_4)_6Mo_7O_{24}.4H_2O$, 20 mg of $CoCl_2.6H_2O$, and 100 mg of $CaCl_2.2H_2O$ in 1 L of water.

The regenerated bacterial layer was replicated in a selective medium prepared by adding thiostrepton and bialaphos (10 mg/L each) to a composition containing 1% glucose, 0.2% L-asparagine, 0.03% NaCl, 0.05% $MgSO_4.7H_2O$, 0.05% $K_2HPO_4$, 0.5% (V/V) the trace element solution, and 1.8% bacto agar, followed by culture at 27° C. for 3 days, to thereby select two clones that grew well.

From the resultant two bialaphos-resistant strains, plasmids were extracted in accordance with a known method ("Current Topics in Microbiology and Immunology" 1982, vol. 96, pp. 69). As a result, the two strains were found to have the same plasmids with a molecular size of about 11.4 kb. These plasmids derived from the two strains were separately cleaved with a restriction enzyme BglII and analyzed by agarose electrophoresis. In both cases, the electrophoresis detected not only the DNA fragment of pIJ703 used in the vector but also an about 5.7-kb DNA fragment. Moreover, the fragments obtained by cleaving the respective plasmids from the two strains with other restriction enzymes (such as SacI, EcoRI, and SmaI) were found to have the same sizes, so that the two plasmids were found to be the same and named plasmid pBRB1. In the case where the hybrid plasmid pBRB1 was introduced into Streptomyces lividans, all the resultant transformants were found to have a resistance to bialaphos. The fact showed that a DNA strand with a molecular size of about 5.7 kb derived from Streptomyces sp. AB3534 in the hybrid plasmid pBRB1 encodes a herbicide-resistance gene.

(4) Determination of a Coding Region of the Herbicide-Resistance Gene

Figure 1:
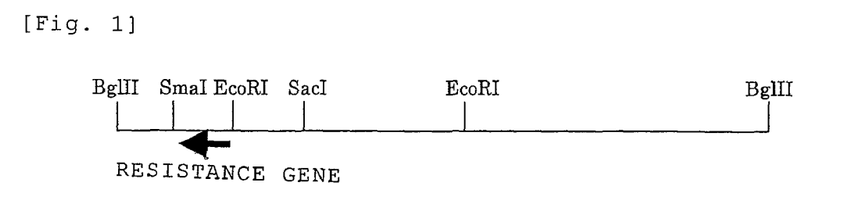
FIG. 1 A restriction enzyme map of a 5.7 kb-BglII fragment that is derived from *Streptomyces* sp. AB3534 strain and contains a DNA strand carrying the herbicide-resistance gene of the present invention.

The coding region of the gene involved in the resistance to herbicides is located in the EcoRI-BglII fragment shown in FIG. 1. The fact was confirmed by examining the resistance to bialaphos of a deletion plasmid prepared from the plasmid pBRB1. That is, it was confirmed by the fact that only a plasmid having an about 1.2-kb EcoRI, BglII fragment in the about 5.7-kb DNA fragment exhibited a resistance to bialaphos. A test for specifically confirming the position of the gene was carried out using a transformation system of Escherichia coli.

The about 1.2-kb EcoRI-BglII fragment that had been confirmed to have a bialaphos-resistance gene was ligated to the EcoRI-BamHI site of a commercially available plasmid vector pUC18, and the resultant plasmid was introduced into Escherichia coli, to thereby yield a transformed Escherichia coli strain having a resistance to bialaphos. A deletion plasmid was prepared by using the SmaI site in the about 1.2-kb EcoRI, BglII fragment and was used to transform Escherichia coli, and as a result, the herbicide-resistance gene of the present invention was confirmed to be present on an about 0.6-kb EcoRI-SmaI fragment. 2 µg of the hybrid plasmid pBRB1 was cleaved with restriction enzymes EcoRI and BglII (20 units each) at 37° C. for 2 hours and subjected to agarose electrophoresis, and only a 1.2 kb-fragment was cut and purified using GeneClean. On the other hand, 2 µg of the plasmid pUC18 was cleaved with EcoRI and BamHI (20 units each) at 37° C. for 2 hours, and the fragments were purified using GeneClean (manufactured by Bio101). The DNA fragments were allowed to react using Takara Ligation kit at 16° C. for 3 hours, to thereby yield a solution of a plasmid obtained by integrating the about 1.2-kb EcoRI, BglII-cleaved DNA fragment into the EcoRI, BamHI-cleaved DNA fragment of the plasmid pUC18. The solution was introduced into competent cells JM109 (manufactured by Takara Bio Inc.). That is, 5 µl of a ligation reaction solution was added to 60 µl of a competent cell solution, and the mixture was subjected to treatments at 0° C. for 30 minutes, at 42° C. for 45 seconds, and at 0° C. for 2 minutes. Then, 500 µl of a SOC solution was added to carry out recovery culture at 36° C. for 1 hour, and the culture solution was spread on an agar medium (LB medium, 1.5% agar, 100 mg/L ampicillin) and cultured at 36° C. 16 hours later, the formed colonies were separated and cultured to isolate a bacterial strain having a plasmid into which the target gene had been inserted, to thereby yield Escherichia coli transformed with a vector (pUC18-B1) obtained by cloning the about 1.2-kb EcoRI, BglII-cleaved DNA fragment derived from pBRB1 into a plasmid pUC18.

The Escherischia coli transformed with pUC18-B1 was found to grow on M9 agar medium (manufactured by GIBCO BRL) containing 1 mM thiogalactopyranoside (IPTG) and 10 mg/L bialaphos. To confirm the further specific position of the gene, the bialaphos-resistance of Escherichia coli transformed with various deletion plasmids of pUC18-B1 having the about 1.2-kb EcoRI, BglII-cleaved fragment was examined, and the results revealed that the herbicide-resistance gene of the present invention is present on a plasmid pUC18-B2 having an about 0.6-kb EcoRI-SmaI fragment. That is, the plasmid pUC18-B1 was cleaved with restriction enzymes EcoRI and SmaI (20 units each) at 37° C. for 2 hours and subjected to agarose electrophoresis, and only a 0.6 kb-fragment was cut and purified using GeneClean. On the other hand, 2 µg of the plasmid pUC18 was cleaved with EcoRI and SmaI (20 units each) at 37° C. for 2 hours, and the fragments were purified using GeneClean (manufactured by Bio101). The DNA fragments were allowed to react using Takara Ligation kit at 16° C. for 3 hours, to thereby yield a solution of the plasmid pUC18-B2 obtained by integrating the about 0.6-kb EcoRI, SmaI-cleaved DNA fragment derived from pBRB1 into the EcoRI, SmaI-cleaved DNA fragment of the plasmid pUC18. The *Escherischia coli* transformed with pUC18-B2 was found to grow on M9 agar medium (manufactured by GIBCO BRL) containing 1 mM thiogalactopyranoside (IPTG) and 10 mg/L bialaphos. Identification of the nucleotide sequence of the about 0.6-kb DNA fragment revealed that the about 0.6-kb fragment contains the nucleotide sequence that is represented by SEQ ID NO: 1 and encodes a protein containing 174 residues represented by SEQ ID NO: 2. The nucleotide sequence was determined by custom DNA sequencing service (Hokkaido System Science Co., Ltd.).

(5) Confirmation of Resistance Mechanism

*Escherichia coli* transformed with pUC18-B2 having the herbicide-resistance gene of the present invention was inoculated into a liquid medium containing 50 ml of LB medium and 50 mg/L ampicillin, and cultured at 37° C. for 1 hour, and 50 µl of a 1 M thiogalactopyranoside solution was added to the culture solution, followed by culture at 37° C. for 3 hours. After completion of the culture, the culture solution was centrifuged at 5,000 rpm for 15 minutes to collect bacterial cells, and the cells were washed once with physiological saline. Then, the washed bacterial cells were suspended in 2 ml of a 20 mM Trisbuffer (pH 8.0) solution and disrupted by ultrasonic waves at 4° C. The solution was centrifuged at 15,000 rpm for 15 minutes to collect the supernatant. The supernatant was diluted 10-fold with 20 mM Tris buffer (pH 8.0) to prepare a crude enzyme solution. Then, 2 µl of the crude solution was added to 98 µl of a reaction solution, and the mixture was allowed to react at 28° C. for 1 hour, followed by measurement of the absorbance at 412 nm to measure the acetylation reaction. The reaction with PPT in the presence of a coenzyme acetyl CoA confirmed that the herbicide-resistance gene of the present invention encodes an enzyme capable of acetylating PPT. The acetylation reaction solution has the composition containing 2 mM DL-phosphinothricin, 0.2 mM Acetyl Coenzyme A (manufactured by Sigma), 0.2 mM 5,5'-dithiobis(2-nitrobenzoic acid) (manufactured by Wako Pure Chemical Industries, Ltd.), and 100 mM Tris buffer (pH 8.0).

The characteristics of the enzyme capable of acetylating PPT of the present invention was analyzed, and the gene of the enzyme was compared to known genes of the enzymes capable of acetylating PPT derived from *Streptomyces hygroscopicus* ("The EMBO Journal" 1987, vol. 6, pp. 2519-2523) and the actinomycete AB2253 strain (JP 2539901 B). The genes of the enzymes capable of acetylating PPT derived from *Streptomyces hygroscopicus* and the actinomycete AB2253 strain were isolated by a known method using total DNA extracted in accordance with the method described in Example 1 (2).

Crude enzyme solutions were extracted from *Escherichia coli* transformed with pUC18-B2 of this Example, pUC19-SH derived from *Streptomyces hygroscopicus*, and pUC19-AB derived from the actinomycete AB2253 strain, which contains the thus-obtained genes of the enzymes capable of acetylating PPT, in the same way as described above, and the characteristics of the acetylation reactions were analyzed. The optimum pH and substrate specificity (Km value) to PPT and a structural homologue thereof, methionine sulfone (MS) were measured, and the results are shown in Table 2. All the enzymes derived from the three strains have PPT-acetylating enzyme activities, but have clearly different optimum pHs and substrate specificities, so the acetylating enzyme gene of the present invention was found to be a novel enzyme gene.

TABLE 2

| Bacterial strain | Vector | Optimum pH | Km value (mM) PPT | Km value (mM) MS |
|---|---|---|---|---|
| *Streptomyces* sp. AB3534 strain (present invention) | pUC18-B2 | 7.5 to 8.5 | 2.46 | 12.98 |
| *Streptomyces hygroscopicus* (control) | pUC19-SH | 6.5 | 0.09 | 106.48 |
| Actinomycete AB2253 strain (control) | pUC19-AB | 8.0 to 8.5 | 14.31 | 2.20 |

Example 2

Introduction of Herbicide-Resistance Gene into Plant Cell (1) Construction of a Vector for Introduction of a Plant Gene In order to express the herbicide-resistance gene derived from *Streptomyces* sp. AB3534 strain in plant cells, PCR was performed using primers having the sequences represented by SEQ ID NOS: 4 and 5 to amplify the herbicide-resistance gene. The reaction solution was prepared by adding water to 5 µl of Takara ExTaq Buffer×10 solution, 4 µl of dNTP mixture, 30 ng of a template DNA, 1 µl each of primer solutions, and 0.5 µl of Takara ExTaq to a total volume of 50 µl. The reactions were performed under conditions of 35 cycles of 94° C. for 30 seconds, 60° C. for 30 seconds, and 72° C. for 45 seconds.

After the reactions, PCR fragments were purified using GeneClean. Restriction enzymes XbaI and SacI (0.5 µl each) and T buffer×10 solution (2 µl) were separately added to the purified PCR fragments and a vector for transforming plant cells, pBI221 (manufactured by Clontech) (0.5 µg each), and water was added to a total volume of 20 µl, followed by a reaction at 36° C. for 16 hours. After the restriction enzyme reactions, the DNA fragments were isolated using GeneClean and used for ligation. That is, 10 µl of Takara Ligation kit-I solution was added to 10 µl of the DNA fragment solution, and the mixture was allowed to react at 16° C. for 1 hour. The solution was introduced into competent cells (DH5α, manufactured by Takara Bio Inc.). That is, 5 µl of the ligation reaction solution was added to 60 µl of a competent cell solution, and the mixture was subjected to treatments at 0° C. for 30 minutes, at 42° C. for 45 seconds, and at 0° C. for 2 minutes. Then, 500 µl of a SOC solution was added to carry out recovery culture at 37° C. for 1 hour, and culture solution was spread on an agar medium (LB medium, 1.5% agar, 100 mg/L ampicillin) and cultured at 37° C. 16 hours later, the formed colonies were separated and cultured to isolate a bacterial strain having a plasmid into which the target gene had been inserted, to thereby prepare a cyclic recombinant vector obtained by ligating the herbicide-resistance gene derived from *Streptomyces* sp. AB3534 to cleaved fragments of a plasmid vector pBI221. The recombinant vector was named p35SHPAT.

The vector p35SHPAT has the herbicide-resistance gene of the present invention which is located downstream of a promoter CaMV35S, and is ligated to NOS terminator at its downstream, and has a size of about 4.2 kbp.

(2) Introduction of a Recombinant Vector into Rice Callus Cells

The recombinant vector p35SHPAT obtained as above was introduced into rice callus cells (see JP 3312867 B).

First, ripe seeds of rice (variety: Nipponbare) were hulled. The resultant seeds were sterilized by immersion in a 70% ethanol solution for 1 minute and then in a 1% (effective chlorine concentration) sodium hypochlorite solution. The thus sterilized rice seeds were placed on a medium prepared by adding 30 g/L sucrose, 2 mg/L 2,4-D as a phytohormone, and 8 g/L agar to known inorganic component composition of MS medium. Incubation was carried out at 28° C. for 45 days with irradiation with light at 2,000 lx for 16 hours per day. The formed calli were cut from the endosperm of the seeds, and those calli having a size of 1 mm or less were obtained in an amount of 3 ml in terms of PCV (Packed Cell Volume) using a stainless steel sieve (mesh size: 1 mm).

5 mg of potassium titanate whiskers LS20 (manufactured by Titan Kogyo K.K.) was put into a 1.5-ml tube, and 1 ml of ethanol was added thereto. The mixture was allowed to stand for 1 hour, and ethanol was removed from the tube and evaporated completely, to thereby yield sterilized whiskers. To this tube containing the whiskers was added 1 ml of sterilized water, followed by sufficient stirring. The whiskers and sterilized water were separated by centrifugation, and the supernatant water was discarded. The whiskers were washed in this manner. Such whisker-washing step was carried out three times. Then, 0.5 ml of known R2 liquid medium was added to the tube, to thereby yield a whisker suspension.

To the tube containing the whisker suspension thus obtained was added 250 μl of the callus having a size of 1 mm or less, followed by stirring. The resultant mixture was centrifuged at 1,000 rpm for 10 seconds to precipitate the callus and whiskers. The supernatant was discarded, to thereby yield a mixture of the callus and whiskers.

To the tube containing the mixture was added 10 μl of the above-described recombinant vector p35SHPAT (10 μg), followed by sufficient mixing and shaking, to thereby yield a uniform mixture.

Next, the resultant uniform mixture in the tube was centrifuged at 18,000×g for 5 minutes. After the centrifugation, the resultant mixture was mixed again by shaking, and this step was repeated three times.

The tube containing the callus cells, whiskers, and recombinant vector carrying the DNA sequence of the present invention obtained as above was placed in a bath of an ultrasonic generator so that the tube was adequately immersed therein. Ultrasonic waves at the frequency of 40 kHz were applied to the tube at the intensity of 0.25 W/cm$^2$ for 1 minute, followed by incubation at 4° C. for 10 minutes. The ultrasonic-treated mixture was washed with the above-mentioned R2 liquid medium, to thereby yield the desired transformed cells introduced with the recombinant vector p35SHPAT.

The callus having the transformed cells, which was obtained by the above-mentioned introduction of the recombinant vector, was put in a 3.5-cm petri dish. Then, 3 ml of a liquid medium which was obtained by adding 30 g/L sucrose and 2 mg/L 2,4-D to the inorganic component composition of R2 medium was added thereto. The callus cells were then cultured on a rotary shaker (50 rpm) at 28° C. with irradiation with light at 2,000 lx for 16 hours per day, to thereby yield dividing cells.

On the third day of culture, 3 ml of the resultant dividing cell suspension was spread evenly over a medium which was prepared by adding 30 g/L sucrose, 2 mg/L 2,4-D, 3 g/L Gelrite, and 3 mg/L bialaphos as a drug for selection to the inorganic component composition of known N6 medium. The cells were cultured at 28° C. for 1 month with irradiation with light at 2,000 lx for 16 hours per day.

After 1 month of culture, a transformed callus which grew healthy on the medium containing bialaphos was selected, to thereby yield rice callus cells transformed by recombinant vector p35HPAT.

(3) Regeneration of Plant Body from Transformed Rice Callus Cells

The transformed cultured cells, which were selected by the above culture based on bialaphos resistance, were transplanted to a medium which was prepared by adding 30 g/L sucrose, 2 mg/L benzyladenine, 1 mg/l naphthalene acetate, 3 g/L Gelrite, and 3 mg/L bialaphos to the inorganic component composition of MS medium. The cells were cultured at 28° C. with irradiation with light at 2,000 lx for 16 hours per day. After 30 days of culture, the resultant regenerated plant body (plumule) was transplanted to a test tube containing MS medium containing 30 g/L sucrose and 3 g/L Gelrite. The transplanted plumule was cultured for 20 days, to thereby yield a transformed rice plant body. As a result, a total of 17 transformants were produced from 3 ml of rice callus. Genomic DNAs were extracted from the 17 rice plant bodies in accordance with a known method ("Cell Engineering, suppl., Protocol of PCR Experiment for Plant" 1995, pp. 30-33, published by Shujunsha Co. Ltd.), and PCR was performed under the conditions described in the (1) above. The results revealed that, in all the cases, about 0.6-kb bands derived from the herbicide-resistance gene were amplified, thereby confirming the presence of the herbicide-resistance gene of the present invention.

(4) Evaluation of Resistance to Herbicide of the Transformed Plant Body

Figure 2:
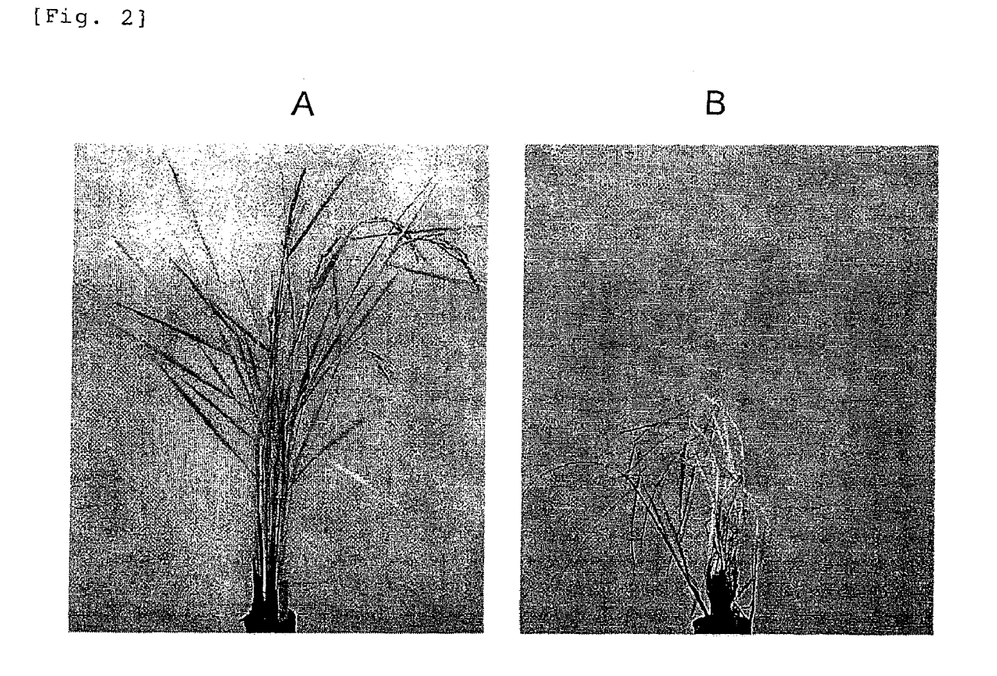
FIG. 2 Figures (pictures) showing growth states two months after spraying a 200-fold diluted solution (treatment concentration during weed growth phase) of a Basta (containing 18.5% PPT) solution (manufactured by Bayer Crop Science) to (A) a recombinant rice plant body introduced with the herbicide-resistance gene of the present invention and (B) a control non-recombinant "Nipponbare" plant body.

In order to evaluate the resistance to herbicides of the plant body carrying the herbicide-resistance gene of the present invention, a commercially available herbicide containing PPT as a major component (Basta solution containing 18.5% of PPT (commercial name, manufactured by Bayer Crop Science) was sprayed in a predetermined concentration (diluted 200-fold, PPT: 0.0925%), and the growth conditions were observed. The recombinant rice plant body obtained as above were acclimated in a closed greenhouse for 2 weeks and cultivated, and the resultant plant body was transferred to an unclosed greenhouse and allowed to continue to grow to about 25 cm in plant length. To the resultant recombinant rice plant body and "Nipponbare" plant body as a control at the same growth stage was sprayed a 200-fold diluted solution of the above-mentioned herbicide (treatment concentration during weed growth phase). After 1 day of spraying, the green color of the leaves of "Nipponbare" as a control started to deteriorate, and the plant was entirely dead after 1 week. On the other hand, the rice plant body modified with the herbicide-resistance gene of the present invention grew healthy. The degrees of leaf blight of the plant bodies after spraying of the herbicide (area ratios (%) of discolored leaves relative to green leaves with respect to total leaves) are shown in Table 3. Meanwhile, in the case of the recombinant rice plant body, normal ear emergence, flowering, and seed setting were observed after 2 months of spraying (FIG. 2).

TABLE 3

| | One day later | Three days later | Five days later | Seven days later |
| --- | --- | --- | --- | --- |
| Recombinant (present invention) | 0 | 0 | 0 | 0 |
| Nonrecombinant (control) | 5 | 30 | 70 | 100 |

The numerical values in the table represent area ratios (%) of discolored leaves relative to green leaves.

INDUSTRIAL APPLICABILITY

The herbicide-resistance gene of the present invention can be used for production of a herbicide-resistant plant body.

The introduction of the herbicide-resistance gene of the present invention to a plant provides a herbicide-resistant plant having an enhanced resistance to herbicides.

What is claimed is:

1. An isolated protein shown in the following (A) or (B):

(A) a protein having the amino acid sequence represented by SEQ ID NO: 2;

(B) a protein having an amino acid sequence of SEQ ID NO: 2 including substitution, deletion, insertion, or addition of 1 to 5 amino acids and having a phosphinothricin acetyltransferase activity.

2. An isolated DNA encoding a protein shown in the following (A) or (B):

(A) a protein having the amino acid sequence represented by SEQ ID NO: 2;

(B) a protein having an amino acid sequence of SEQ ID NO: 2 including substitution, deletion, insertion, or addition of 1 to 5 amino acids and having a phosphinothricin acetyltransferase activity.

3. The isolated DNA according to claim 2, which is shown in the following (A) or (B):
   (A) a DNA having nucleotides 68 to 592 in the nucleotide sequence represented by SEQ ID NO: 1;
   (B) a DNA hybridizing with a DNA having nucleotides 68 to 592 in the nucleotide sequence represented by SEQ ID NO: 1 under stringent conditions that allow hybridization in a hybridization solution of 500 mM NaPi buffer (pH 7.2), 7% SDS, 1 mM EDTA at 68° C.

4. A recombinant vector, comprising the DNA according to claim 2 or 3.

5. A transformed plant cell, which is transformed by the DNA according to claim 2 or 3.

6. A transformed plant, which is transformed by the DNA according to claim 2 or 3.

7. A seed comprising said DNA, which is obtained from the transformed plant according to claim 6.

8. A herbicide-resistant plant body, which is transformed with the DNA according to claim 2 or 3 and exhibits a resistance to herbicides by expressing the DNA.

9. A transformed plant cell, which is transformed by the recombinant vector according to claim 4.

10. A transformed plant, which is transformed by the recombinant vector according to claim 4.

11. A seed comprising said recombinant vector, which is obtained from the transformed plant according to claim 10.

12. A herbicide-resistant plant body, which is transformed with the recombinant vector according to claim 4, and exhibits a resistance to herbicides by expressing the DNA in the recombinant vector.

* * * * *